United States Patent [19]

Faraj

[11] Patent Number: 5,292,974
[45] Date of Patent: Mar. 8, 1994

[54] ALKYLENE OXIDE ISOMERIZATION PROCESS AND CATALYST

[75] Inventor: Mahmoud K. Faraj, Newtown Square, Pa.

[73] Assignee: ARCO Chemical Technology, L.P., Wilmington, Del.

[21] Appl. No.: 98,080

[22] Filed: Jul. 28, 1993

Related U.S. Application Data

[62] Division of Ser. No. 879,673, May 6, 1992, abandoned.

[51] Int. Cl.$^5$ .................. C07C 29/56; C07C 33/03
[52] U.S. Cl. ........................ 528/908; 502/208
[58] Field of Search .......................... 568/908

[56] References Cited

U.S. PATENT DOCUMENTS

| | | | |
|---|---|---|---|
| 3,044,850 | 7/1962 | Denton | 23/107 |
| 3,090,815 | 5/1963 | Denton | 260/632 |
| 3,090,816 | 5/1963 | Denton | 260/632 |
| 3,092,668 | 6/1963 | Bruson et al. | 260/632 |
| 3,238,264 | 3/1966 | Rowton | 568/908 |
| 3,274,121 | 9/1966 | Schneider | 252/437 |
| 3,285,967 | 11/1966 | Schaffer | 502/208 |
| 4,065,510 | 12/1977 | Schreyer et al. | 502/208 |
| 4,720,598 | 1/1988 | Scholte | 568/908 |

FOREIGN PATENT DOCUMENTS

| | | | |
|---|---|---|---|
| 62-22736 | 1/1987 | Japan . | |
| 2023439 | 1/1987 | Japan | 502/208 |
| 1-272539 | 10/1989 | Japan . | |
| 1242135 | 8/1971 | United Kingdom | 502/208 |

*Primary Examiner*—Joseph E. Evans
*Attorney, Agent, or Firm*—Jonathan L. Schuchardt

[57] ABSTRACT

An improved alkylene oxide isomerization catalyst and process are disclosed. The catalyst comprises lithium phosphate and a neutral inorganic support. A key feature of the invention is that the lithium phosphate is distributed homogeneously and principally on the surface of the support. The catalyst exhibits exceptionally high productivities in the conversion of propylene oxide to allyl alcohol.

9 Claims, 9 Drawing Sheets

ALKYLENE OXIDE ISOMERIZATION PROCESS AND CATALYST

This is a division of application Ser. No. 07/879,673, filed May 6, 1992, now allowed.

FIELD OF THE INVENTION

The invention relates to processes for isomerizing alkylene oxides to allylic alcohols, and more particularly, to alkylene oxide isomerization processes that employ supported basic lithium phosphate catalysts.

BACKGROUND OF THE INVENTION

The discovery that alkylene oxides rearrange to give allylic alcohols in the presence of basic lithium phosphate catalysts sparked years of industrial research aimed at improving catalyst lifetime and productivity. Allyl alcohol, the simplest allylic alcohol, is produced by isomerizing propylene oxide. Allyl alcohol is converted to useful allyl derivatives or is modified to give 1,4-butanediol and its derivatives.

Two general isomerization processes are known: the gas-phase process (see for example, U.S. Pat. Nos. 3,044,850 and 4,720,598) and the slurry-phase process (e.g., U.S. Pat. No. 3,274,121). In the gas-phase process, the alkylene oxide is passed through supported or unsupported lithium phosphate at elevated temperatures, and the allylic alcohol is recovered and purified by distillation. A major drawback of the gas-phase process is that nonvolatile by-products accumulate on the catalyst surface over time and rapidly stifle catalyst activity.

The slurry-phase process, which is practiced commercially, was developed to overcome the catalyst deactivation problems of the gas-phase process. In the slurry-phase process, lithium phosphate is suspended in a high-boiling oil. During the reaction, a portion of the catalyst suspension is continuously removed and centrifuged to separate the tar-containing oil from the catalyst. Tars are distilled from the oil, the lithium phosphate is washed with acetone, and the purified catalyst components are recycled to the reactor. Major problems with the slurry-phase process include catalyst loss and high oil consumption (about 15 pounds of oil per 1000 pounds of allyl alcohol produced).

Low catalyst productivity is a problem common to both the gas- and slurry-phase isomerization processes. In spite of many efforts to improve productivity by varying the catalyst preparation method or process conditions, only marginal productivity improvements have resulted. The best processes known have catalyst productivities less than or equal to about 1.5 kilograms of allylic alcohol produced per kilogram of lithium phosphate per hour (see, for example, U.S. Pat. No. 3,274,121).

U.S. Pat. No. 4,720,598 teaches that high surface area lithium phosphate supported on α-alumina is an effective catalyst for gas-phase isomerization of propylene oxide to allyl alcohol. The reference stresses the need to slowly combine lithium hydroxide and phosphate salts during lithium phosphate preparation. At high lithium phosphate loading (78 wt. % $Li_3PO_4$, 22 wt. % α-alumina) conversion of propylene oxide is 50-60%. Selectivity to allyl alcohol is good (88%), but the low productivity achieved (about 1 kg allyl alcohol per kg lithium phosphate per hour) is comparable to what can be achieved with the slurry process. Catalysts with lower lithium phosphate loadings are not shown, and the reference is silent regarding the amounts of 1-propanol and other by-products generated. 1-Propanol is extremely difficult to separate from allyl alcohol by distillation because both compounds boil at about 97° C.

Improved isomerization catalysts are needed. Preferably, the catalysts are useful in a gas-phase isomerization process, since the gas-phase process is simpler and eliminates the problems of treatment and disposal of contaminated oil. A high-activity catalyst and economical process for making allyl alcohol from propylene oxide at high production rates with good selectivity to allyl alcohol is especially needed. A catalyst that has a long lifetime and is capable of regeneration is desirable.

SUMMARY OF THE INVENTION

The invention is an efficient catalyst for isomerizing an alkylene oxide to an allylic alcohol. The catalyst comprises lithium phosphate and a neutral inorganic support. An important feature of the catalyst is that the lithium phosphate is distributed homogeneously and principally on the surface of the neutral inorganic support. Catalysts of the invention uniquely exhibit productivities greater than about 2 kilograms of allylic alcohol per kilogram of lithium phosphate per hour, and remarkably, several times higher than the best catalysts currently known in the art. Supported catalysts previously used in the art typically had lithium phosphate contents greater than about 70 weight percent. I have now found that the most productive catalysts comprise from about 5 to about 60 percent by weight of lithium phosphate and from about 40 to about 95 percent by weight of the neutral inorganic support. These catalysts contain a minimum amount of free, unsupported lithium phosphate.

The invention also includes a process for isomerizing an alkylene oxide to an allylic alcohol. The process comprises heating the alkylene oxide in the presence of the supported lithium phosphate catalyst described above. The catalyst and process of the invention are well-suited to the commercial production of allyl alcohol from propylene oxide.

The invention also includes a method for preparing the catalyst.

BRIEF DESCRIPTION OF THE DRAWINGS

FIGS. 1A-9A are photomicrographs of supported lithium phosphate catalysts.

FIGS. 1B-9B are phosphorus-mapping photomicrographs, which show how the lithium phosphate is distributed on the support. Table 5 summarizes the catalysts pictured in the photomicrographs.

DETAILED DESCRIPTION OF THE INVENTION

Figure 1A:
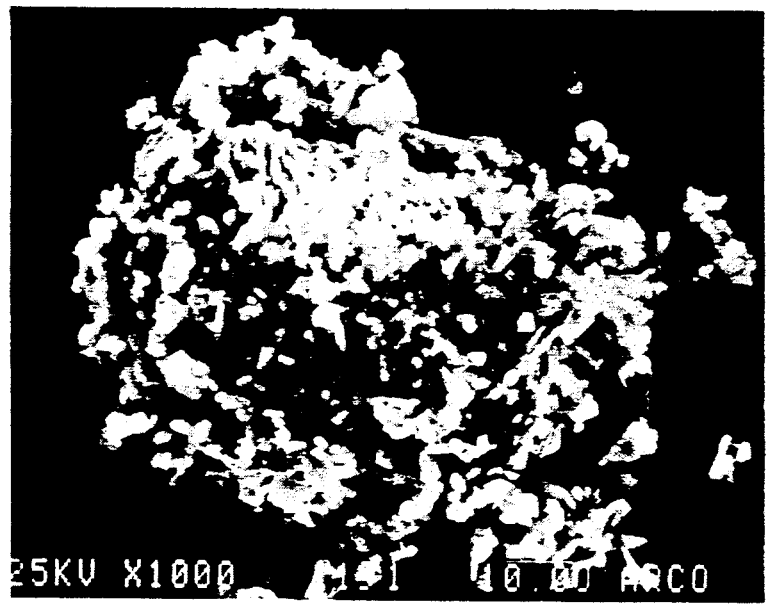
Figure 1B:
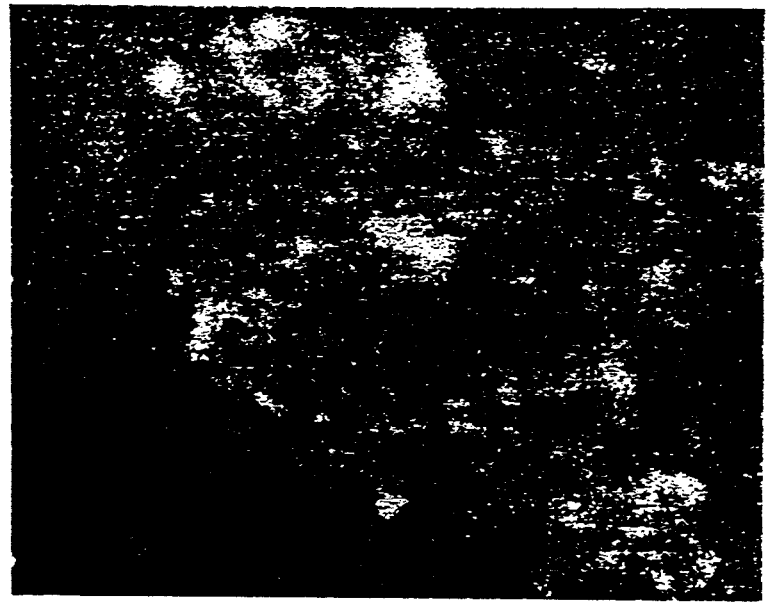
Figure 2A:
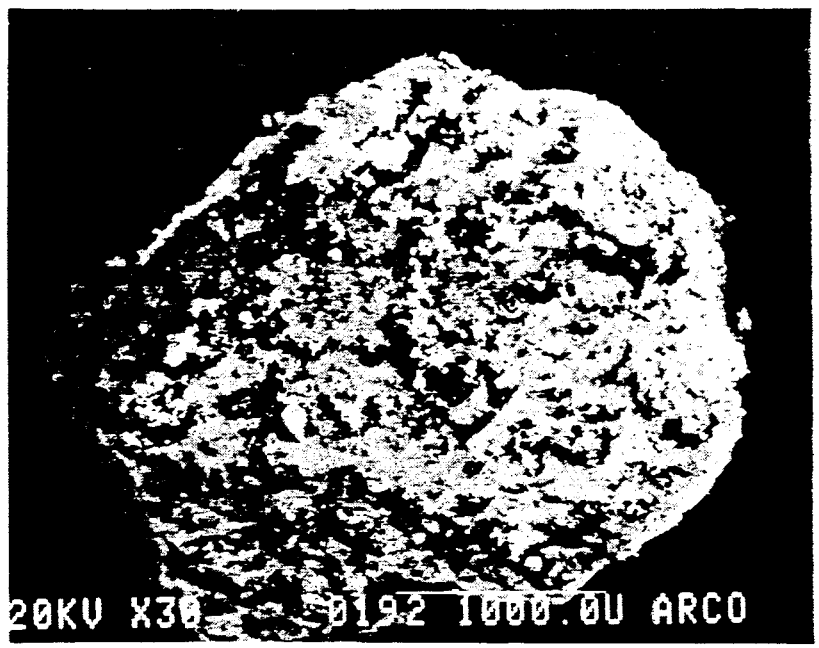
Figure 2B:
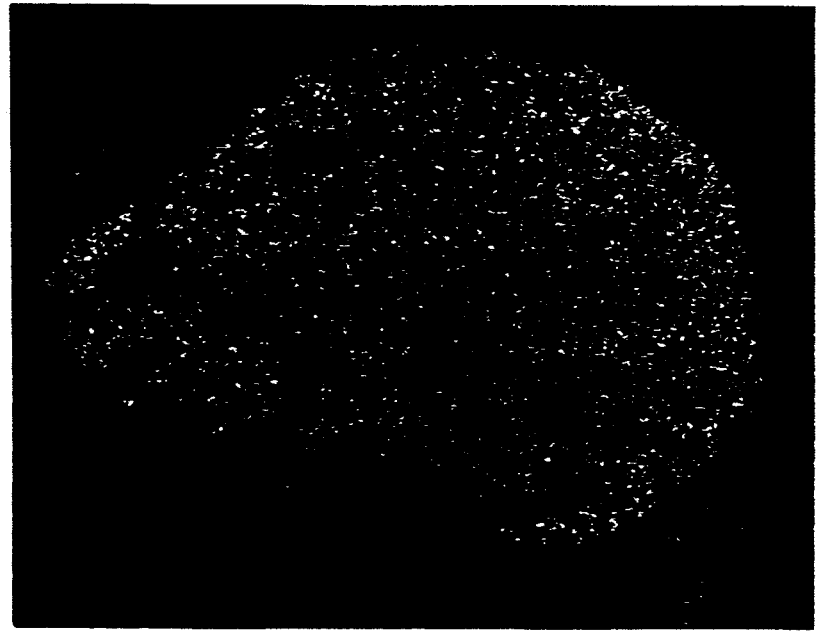
Figure 3A:
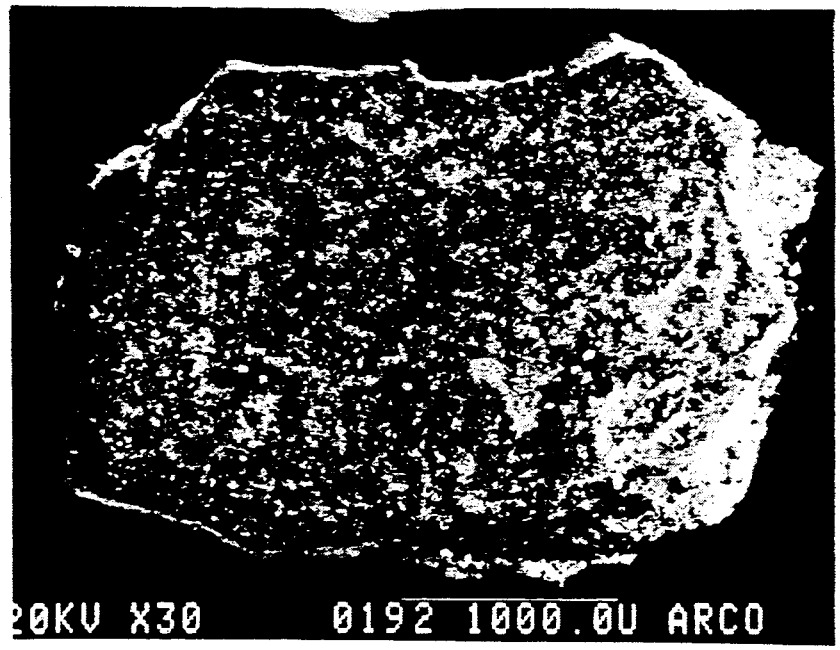
Figure 3B:
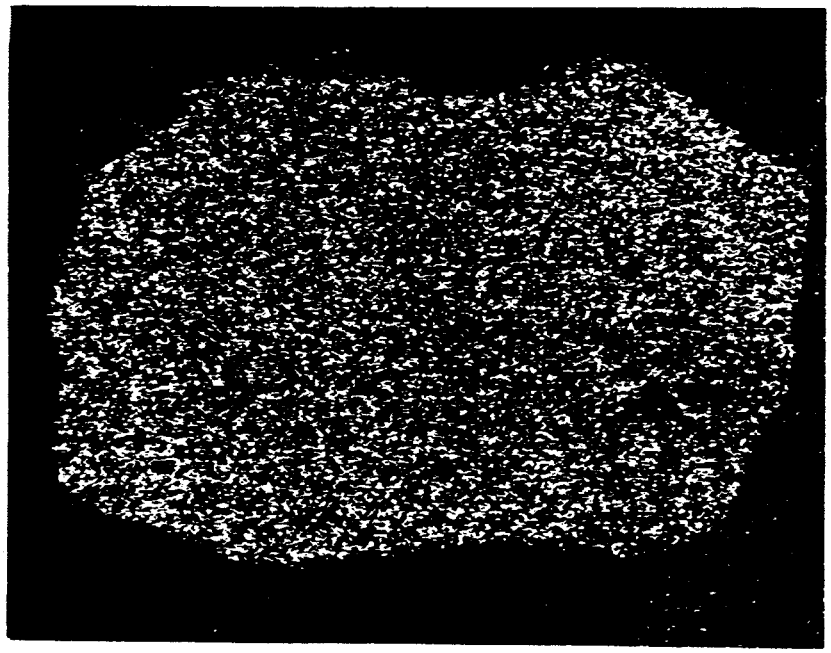
Figure 4A:
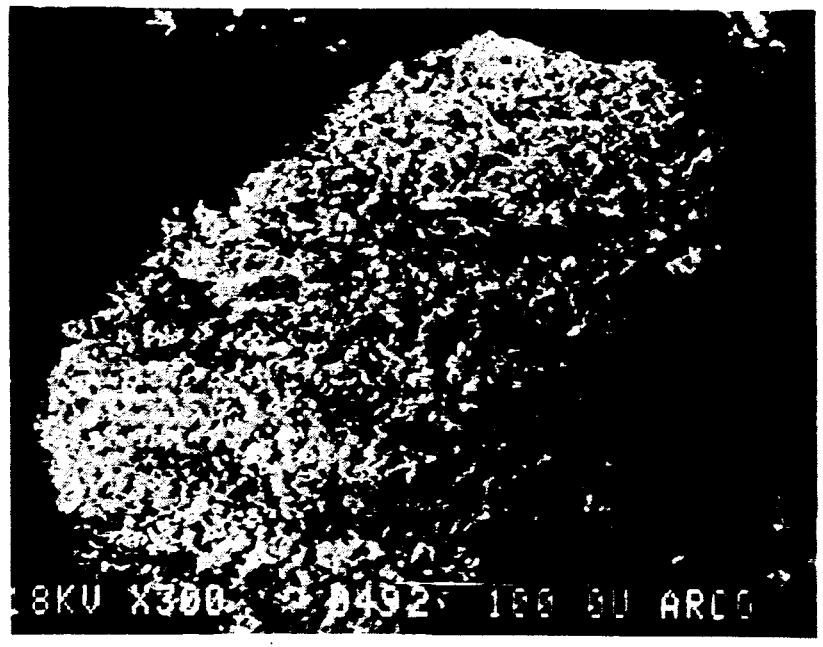
Figure 4B:
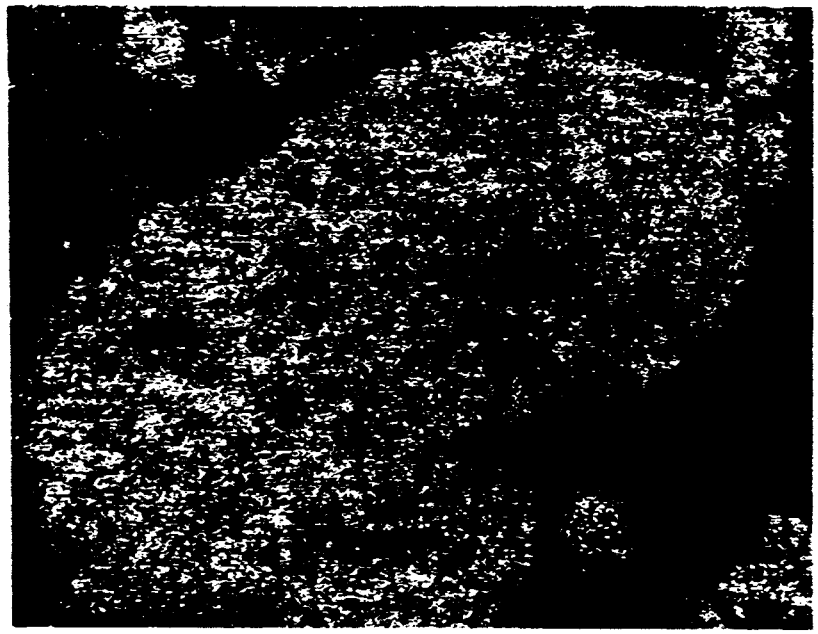

The catalyst of the invention allows efficient isomerization of alkylene oxides to allylic alcohols. The catalyst comprises lithium phosphate and a neutral inorganic support.

The lithium phosphate useful for preparing the catalyst of the invention is commonly referred to as "basic lithium phosphate," and is preferably prepared in a strongly basic (pH>13) medium. Numerous methods are known in the art for preparing basic lithium phosphate, and any of these methods is suitable for preparing basic lithium phosphate for the catalyst of the invention. Suitable preparations of lithium phosphate are described, for example, in U.S. Pat. Nos. 3,044,850, 3,274,121, and 4,720,598, the complete teachings of which are incorporated herein by reference.

Generally, an aqueous solution containing a soluble lithium salt (e.g., lithium hydroxide, lithium nitrate, lithium acetate, lithium formate, or the like) is combined at any desired rate with an aqueous solution of phosphoric acid and/or one or more salts of phosphoric acid. The resulting precipitate of basic lithium phosphate is recovered by any convenient means such as filtration or centrifugation. Preferably, the lithium phosphate is washed with water to reduce its alkalinity, and is then dried.

One way to prepare suitable lithium phosphate for use in the invention is described in Example 1. Aqueous solutions of sodium phosphate and lithium/sodium hydroxide are simply combined, and the precipitate is filtered, washed, dried, and calcined. This catalyst has a lithium/phosphorus ratio within the range of about 3.0 to about 3.4, excess hydroxide within the range of about 0 to about 0.40 moles per mole of lithium phosphate, and a surface area within the range of about 20 to about 50 $m^2/g$. Less than 3 wt. % of the particles have a particle size less than 4 microns.

Lithium phosphate is also commercially available from numerous sources, including Cypress Foote Mineral, Rhone-Poulenc, Lithco, and many other suppliers. These are typically suitable for preparing catalysts of the invention.

The catalyst of the invention includes a neutral inorganic support. Any inorganic support that is essentially neutral can be used. Suitable supports include diatomaceous earth, activated carbon, clays, silicas, $\alpha$-alumina, silica-aluminas, zeolites, phosphorus-containing silicates or aluminosilicates, and the like, and mixtures thereof. Silica-aluminas of any silicon/aluminum ratio can be used. Normally acidic supports can be made sufficiently neutral for use in the invention by proton exchange with basic materials. For example, acid clays such as montmorillonite can be washed with aqueous sodium hydroxide to prepare a support that is sufficiently neutral for use in the invention. Residual acidity of the support should be less than about 0.2 meq/g. Preferred supports are $\alpha$-alumina and high surface area aluminosilicates such as alkali metal-exchanged mordenites and alkali metal-exchanged Y-zeolites.

An example of a suitable $\alpha$-alumina support for use in the invention is "A-14" $\alpha$-alumina (product of ALCOA), which has a surface area of about 0.7 $m^2/g$. Other neutral $\alpha$-aluminas are suitable. Suitable alkali metal-exchanged Y-zeolites are available under the "VALFOR" trademark from PQ Corporation. "VALFOR CP300-63" Na-Y-zeolite, which has a silica/alumina mole ratio of 5.3, a sodium oxide content of 12.9 wt. %, and a surface area of 900 $m^2/g$, is one example of a suitable sodium-exchanged Y-zeolite. Suitable alkali metal-exchanged mordenites are available from Conteka. "CBV-10A" sodium-exchanged mordenite, which has a silica/alumina ratio of 12, a sodium oxide content of 6.9 wt. %, and a surface area of 450 $m^2/g$, is one example of a suitable sodium-exchanged mordenite. Other neutral alkali-metal exchanged mordenites and Y-zeolites are also suitable.

Strongly basic supports such as calcium oxide, magnesium oxide, and the like, and strongly acidic supports such as $\gamma$-alumina, are generally unsuitable for use in the invention because they tend to give catalysts with low productivities and poor allylic alcohol selectivities (see Comparative Examples 8-10).

The lithium phosphate and the neutral inorganic support can be combined in any desired proportion. For a highly productive catalyst, however, it is important to distribute the lithium phosphate homogeneously and principally on the surface of the support. If too little lithium phosphate is used, a homogeneous distribution of lithium phosphate is not achieved, and catalyst activity is poor. If too much lithium phosphate is used, the support surface becomes saturated, and the excess portion of the lithium phosphate will be unsupported. I have found that catalysts having a significant amount of unsupported lithium phosphate exhibit relatively low productivities.

It is preferred to use an amount of lithium phosphate within the range of about 5 to about 60 weight percent, and an amount of the neutral support within the range of about 40 to about 95 weight percent based on the weight of the supported catalyst. When the amount of lithium phosphate is within this range, scanning electron micrographs (particularly the phosphorus-mapping experiments) indicate that the lithium phosphate is homogeneously distributed on the surface of the catalyst, and little excess, unsupported lithium phosphate is present. These catalysts exhibit productivities greater than about 2 kg of allylic alcohol per kg of lithium phosphate per hour. A more preferred catalyst comprises from about 25 to about 40 weight percent of lithium phosphate and from about 60 to about 75 weight percent of the neutral inorganic support based on the amount of supported catalyst.

The supported lithium phosphate catalyst is preferably prepared as follows. Lithium phosphate, a neutral inorganic support, and water are combined and mixed well. The mixture is filtered to isolate the solids. The solids are then washed, dried, and calcined to give the supported catalyst. Examples 2–4 illustrate this technique. Any suitable method for supporting the lithium phosphate on the neutral inorganic support can be used.

A suitable supported catalyst can also be prepared by generating the basic lithium phosphate in the presence of the neutral inorganic support provided that the neutral support is stable under the conditions used to prepare the lithium phosphate.

If desired, solid basic lithium phosphate can simply be physically mixed with the neutral inorganic support, but it is preferred to deposit the lithium phosphate on the surface of the support from an aqueous mixture.

The invention also includes a process for isomerizing an alkylene oxide to an allylic alcohol. The process comprises heating the alkylene oxide in the presence of the supported catalyst described above. The process may be a gas- or slurry-phase process, although the catalyst is most suitable for a gas-phase process.

The alkylene oxides useful in the process of the invention are those capable of rearranging to give an allylic alcohol. Examples of suitable alkylene oxides include, but are not limited to, propylene oxide, 1,2-epoxybutane, 1,2-epoxypentane, 1,2-epoxyheptane, 1,2-epoxyoctane, and the like, and mixtures thereof. Propylene oxide, which rearranges to give allyl alcohol, is preferred.

The process of the invention is performed at elevated temperatures, typically within the range of about 150° C. to about 400° C. A preferred range is from about 180° C. to about 360° C. Most preferred is the range from about 270° C. to about 320° C.

If desired, an inert gas may be used as a diluent for the alkylene oxide in the process. Thus, for example, a mixed vapor stream of propylene oxide and nitrogen can be fed to the reaction zone. Suitable inert gases include nitrogen, argon, helium, and the like, and mixtures thereof.

The process of the invention can be performed at any suitable pressure, and is most conveniently performed at or slightly above atmospheric pressure.

Other particulars of the process design and apparatus will be apparent to those skilled in the art.

The process of the invention is characterized by good alkylene oxide conversions (typically about 50% or greater), high allylic alcohol selectivities (typically greater than 85%), and unusually high productivities (greater than 2 kg allylic alcohol per kg $Li_3PO_4$ per hour). Selectivity to n-propanol is low (less than 1%) when propylene oxide is isomerized. In contrast to gas-phase processes previously known in the art, the process of the invention is characterized by excellent catalyst lifetimes (see Examples 21–22). The catalysts of the invention can be regenerated readily by conventional methods such as calcination.

The following examples merely illustrate the invention. Those skilled in the art will recognize numerous variations that are within the spirit of the invention and scope of the claims.

EXAMPLE 1

Preparation of Basic Lithium Phosphate

Sodium phosphate dodecahydrate (380 g) is dissolved in one liter of hot water (50°–60° C.). A solution prepared from sodium hydroxide (40 g), lithium hydroxide monohydrate (141.9 g), and one liter of hot water is rapidly combined with the sodium phosphate solution. The mixture is stirred for 1 h at 50°–60° C. The mixture is filtered, and the white precipitate of lithium phosphate is washed with hot water (4×800 mL) until the pH of the water wash is about 12. The lithium phosphate is dried under vacuum (120° C., 6 h) and calcined (300° C., 8 h minimum) to give 106 g (91%) of catalyst.

EXAMPLE 2

Preparation of Lithium Phosphate/Na-Y-Zeolite Catalyst

Lithium phosphate (30 g, from Example 1) is combined with "VALFOR CP300-63" sodium-exchanged Y-zeolite (50 g, product of PQ Corporation) and one liter of hot water (50°–60° C.). After 2 h of stirring, the mixture is filtered, washed with hot water (4×400 mL), vacuum dried (120° C., 6 h), and calcined (300° C., 18 h). The yield of supported catalyst is 64 g.

EXAMPLE 3

Preparation of Lithium Phosphate/Na-Exchanged Mordenite Catalyst

The procedure of Example 2 is followed with 50 g of "CBV-10A" sodium-exchanged mordenite (product of Conteka) in place of the Y-zeolite. The yield of supported catalyst is 70 g.

EXAMPLE 4

Preparation of Lithium Phosphate/α-Alumina Catalyst

The procedure of Example 2 is followed with 50 g of "A-14" α-alumina (product of ALCOA) in place of the Y-zeolite. The yield of supported catalyst is 78 g.

EXAMPLES 5–10

Gas-Phase Isomerization of Propylene Oxide Using Supported Lithium Phosphate Catalysts Lithium phosphate is prepared and deposited on various acidic, basic, and neutral supports using the methods of Examples 1–4. Each of the supported catalysts contains 37 wt. % lithium phosphate. Each supported catalyst is used to isomerize propylene oxide to allyl alcohol as described below.

Propylene oxide is slowly pumped into a vaporization zone (200°–250° C.) using a liquid chromatography pump. The vaporized propylene oxide stream is combined with a stream of nitrogen and the gaseous mixture is passed through a cylindrical column of the supported catalyst at 300° C. The feed rate of propylene oxide vapor is adjusted to maintain a constant weight hourly space velocity (WHSV) value between 2 and 3. The reaction products are condensed at −6° C. and analyzed by gas chromatography.

As shown in Table 1, good propylene oxide conversions (55–73%), high allyl alcohol selectivities (87–89%), and excellent productivities (3–4 kg allyl alcohol per kg of lithium phosphate per hour) are achieved with 37% lithium phosphate on neutral supports (Examples 5–7), i.e., α-alumina, sodium-exchanged Y-zeolite, and sodium-exchanged mordenite. In contrast, lithium phosphate on acidic supports such as γ-alumina (Comparative Example 10) and basic supports such as magnesium oxide (Comparative Example 8) and calcium oxide (Comparative Example 9) give relatively low conversions and productivities. The amount of 1-propanol generated as a by-product also decreases to less than 1% when a neutral support is used.

EXAMPLES 11–17

Gas-Phase Isomerization of Propylene Oxide Effect of Lithium Phosphate Loading—α-Alumina Support Lithium phosphate supported on "A-14" α-alumina is prepared as described in Examples 1 and 4, but the amount of lithium phosphate is varied between 0 and 77 wt. %.

Propylene oxide is isomerized to allyl alcohol according to the method of Examples 5–10 using each of the seven catalysts, which have lithium phosphate contents of 0, 12.5, 25, 37, 50, 62.5, and 77 wt. %.

As shown in Table 2, high allyl alcohol selectivities (87–91%), low 1-propanol selectivities (0.7–0.9%), and high productivities (2.4 to 4.6) are achieved at lithium phosphate loadings between 12.5 and 50 wt. %. These results are surprising in view of the fact that the most productive catalysts known in the art have characteristically high loadings (greater than about 70% lithium phosphate).

Figure 5A:
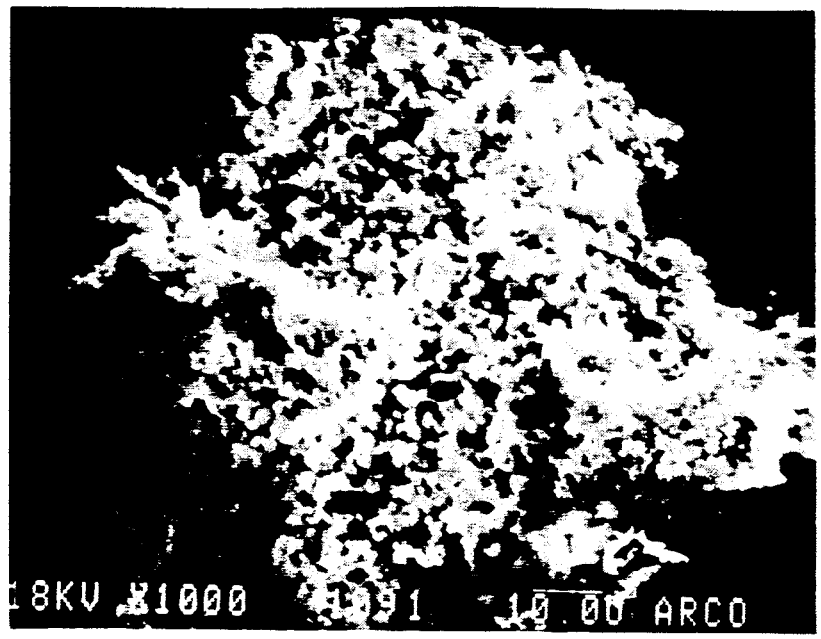
Figure 5B:
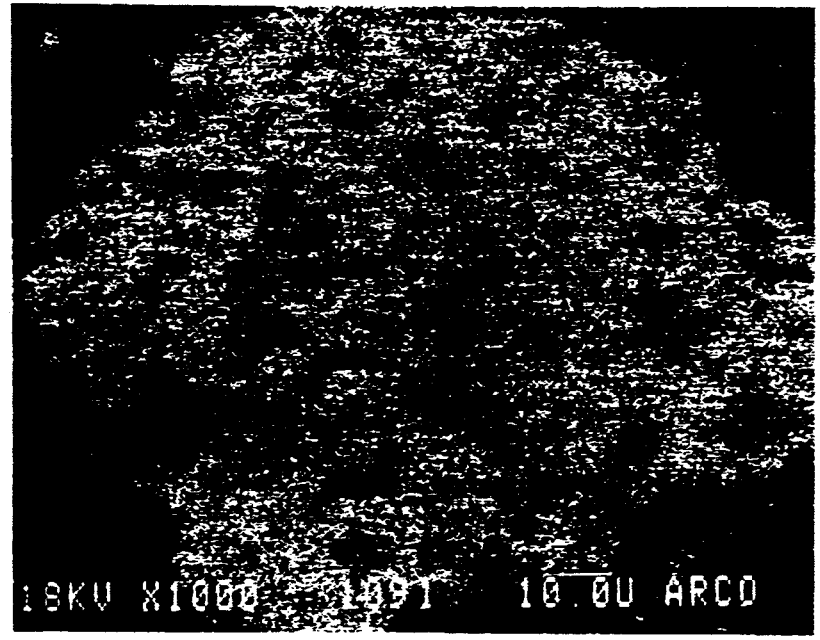
Figure 6A:
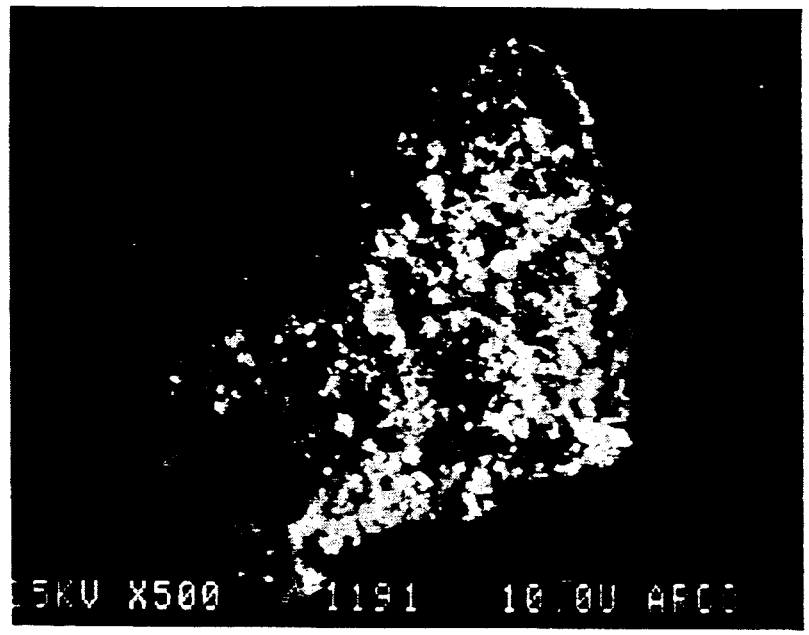
Figure 6B:
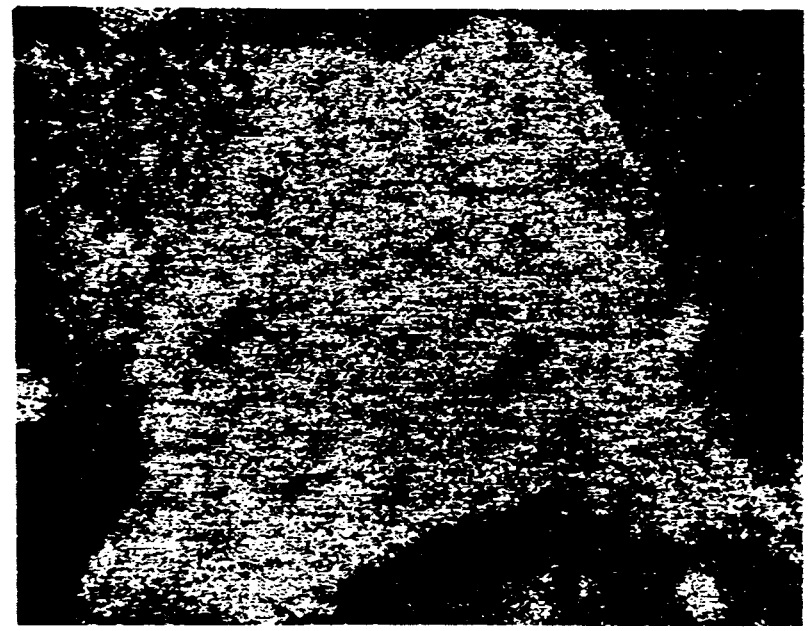
Figure 7A:
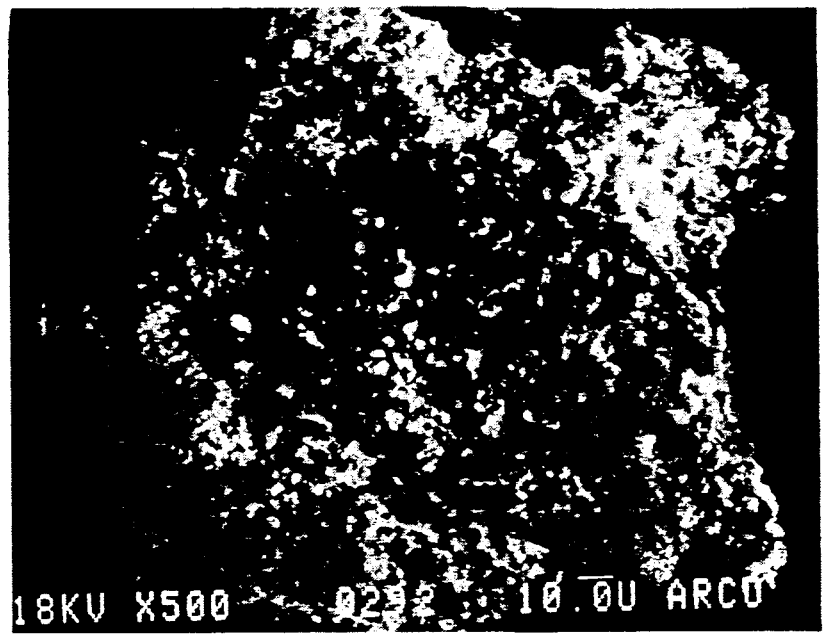
Figure 7B:
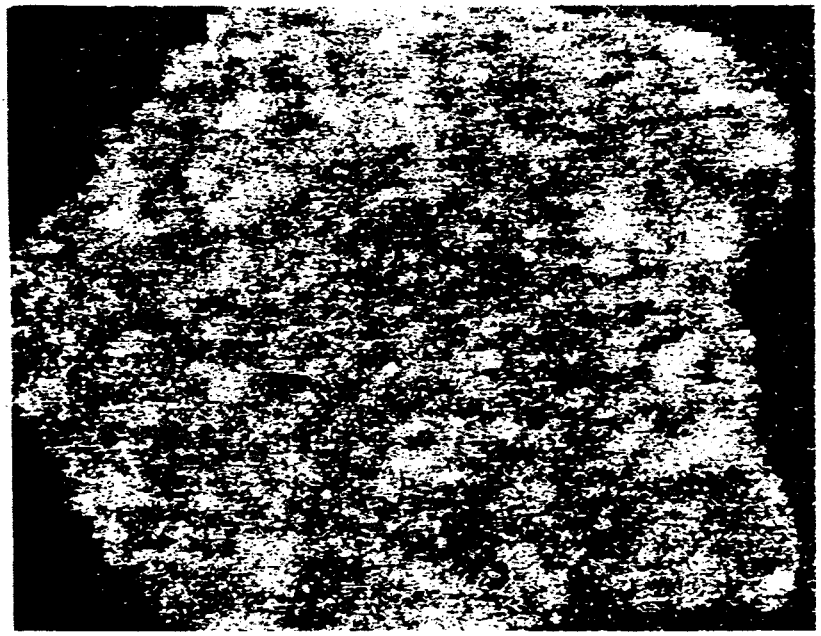
Figure 8A:
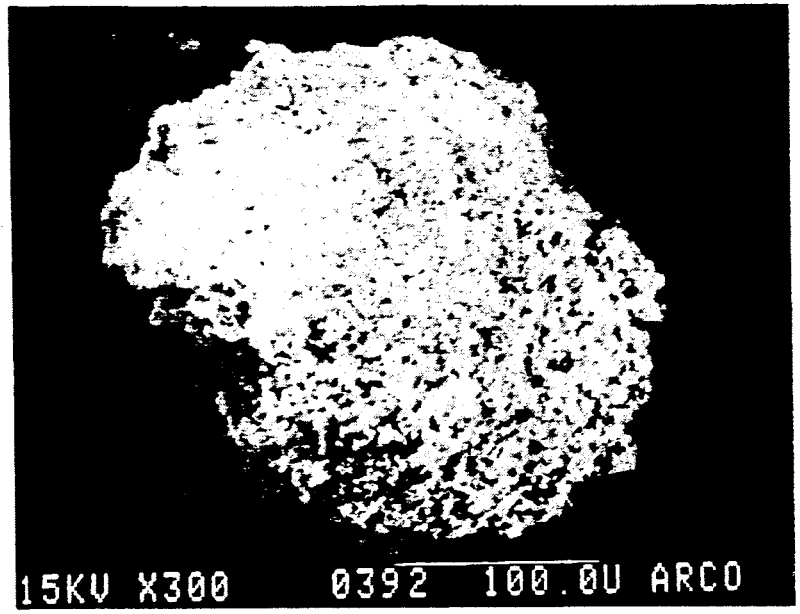
Figure 8B:
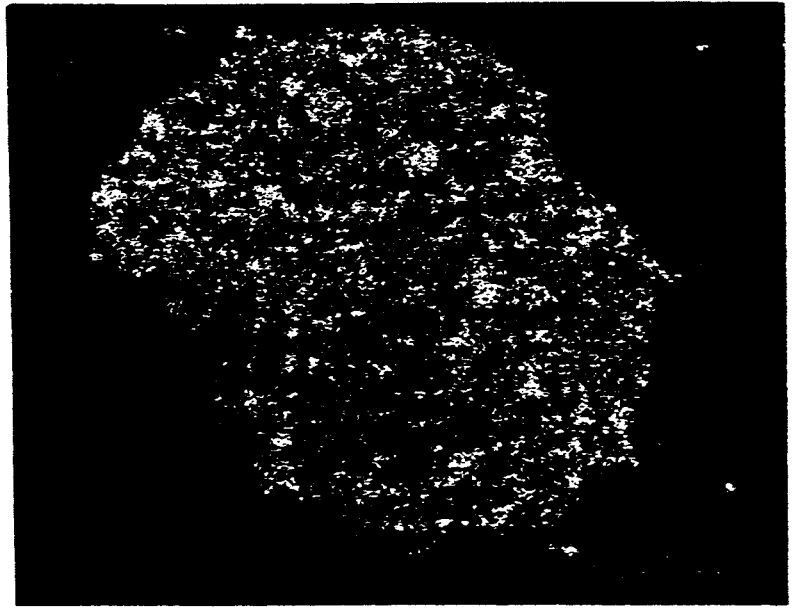
Figure 9A:
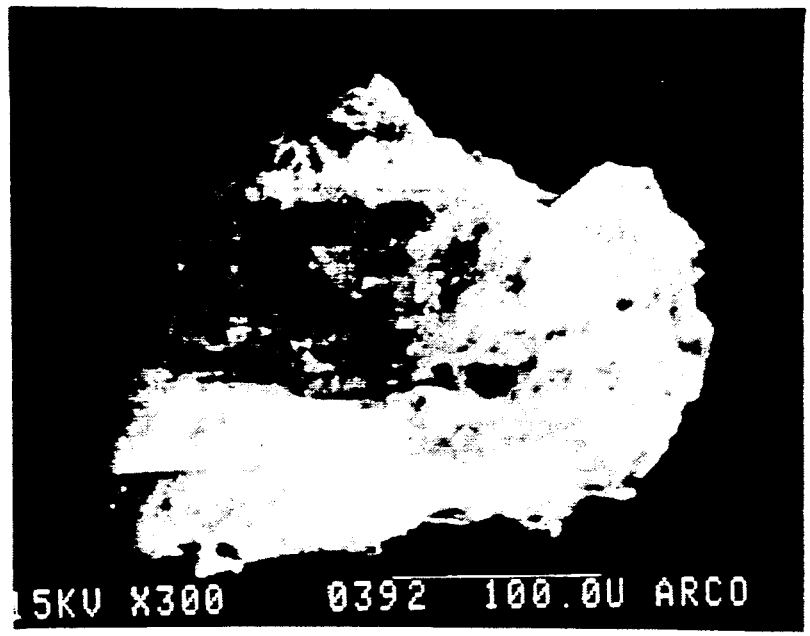
Figure 9B:
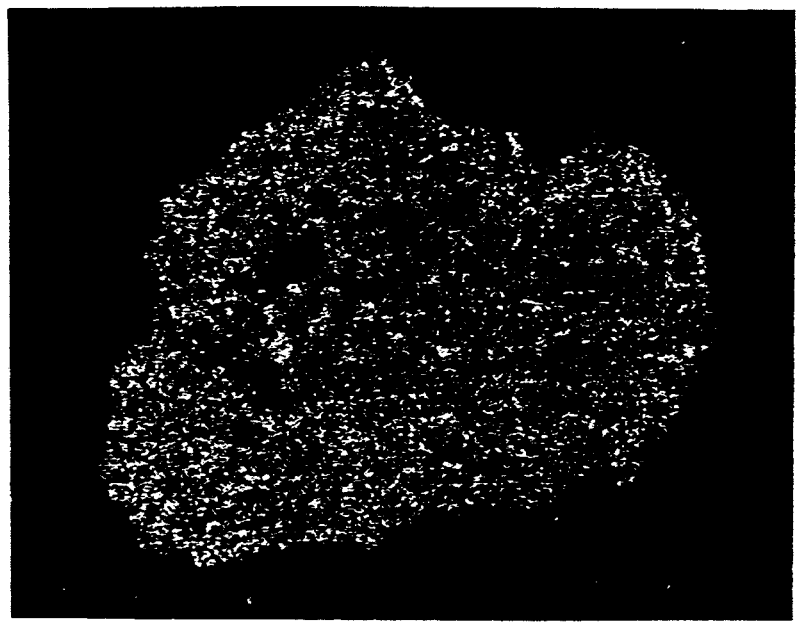

Scanning electron micrographs (SEM) of the supported catalysts (FIGS. 1A–9A and 1B–9B) indicate that the lithium phosphate is homogeneously distributed on the support when the amount of lithium phosphate is within the range of 12.5 to about 50 percent by weight based on the weight of the supported catalyst; the amount of excess, unsupported lithium phosphate is minimal. Since this is the loading range that also gives catalysts with excellent activity and productivity, there is an apparent connection between homogeneity and productivity. At higher loadings, such as 77% lithium phosphate (see U.S. Pat. No. 4,720,598), productivity diminishes. The SEMs of the 77% wt. % Li₃PO₄ catalyst indicate that the surface sites available for the lithium phosphate are saturated, and excess unsupported lithium phosphate is present (Compare FIGS. 6A and 6B). Without wishing to be bound by any theory, I believe that this excess lithium phosphate in the 77% $Li_3PO_4$ catalyst makes the catalyst less stable and less active than those prepared at lower lithium phosphate loadings. In contrast, the SEMs for the catalysts having 12.5, 25, 37, and 50 wt. % $Li_3PO_4$ (FIGS. 1A-4A and 1B-4B) show that the lithium phosphate resides principally on the surface of the support. Apparently, interaction between the lithium phosphate and the support is more intimate in the 12.5-50 wt. % $Li_3PO_4$ range. The catalyst having 62.5 wt. % $Li_3PO_4$ (FIGS. 5A and 5B) represents a "borderline" example; the SEM shows less free $Li_3PO_4$ compared with the 77 wt. % catalyst, but productivity of the two catalysts is about the same (see Table 2, Comparative Examples 16 and 17).

EXAMPLES 18-20

Gas-Phase Isomerization of Propylene Oxide Effect of $Li_3PO_4$ Loading—Sodium-exchanged Y-Zeolite Support The procedure of Examples 5-10 is followed, except that a lithium phosphate catalyst supported on "VALFOR CP300-63" sodium-exchanged Y-zeolite is used (see Examples 1 and 2).

The results from gas-phase isomerization experiments using this supported catalyst appear in Table 3. Excellent allyl alcohol selectivities (80-90%), low 1-propanol selectivities (0.4-0.8%), and high productivities (3.0-5.0) are obtained at lithium phosphate loadings of 25-50 wt. %.

EXAMPLES 21-22

Catalyst Lifetime Experiments

EXAMPLE 21

Gas-phase isomerization of propylene oxide as previously described is performed, but the process is carried out continuously for 120 hours. No decline in catalyst activity is observed. The catalyst used contains 37 wt. % $Li_3PO_4$ on "A-14" α-alumina. The feed rate of propylene oxide corresponds to a WHSV of 2.3 h⁻¹. After 120 hours, conversion of propylene oxide is 56%, and selectivity to allyl alcohol is 89%.

EXAMPLE 22

Lithium phosphate supported on sodium-exchanged Y-zeolite is prepared as follows. The procedure of Example 1 is used to prepare basic lithium phosphate, except that lithium nitrate (233.5 g) is used in place of lithium hydroxide monohydrate. The yield of lithium phosphate is 100 g (86%). The pH of the final water wash is 11.5. The procedure of Example 2 is followed to support the lithium phosphate on "VALFOR CP300-63" sodium-exchanged Y-zeolite.

The procedure of Example 21 is followed to isomerize propylene oxide to allyl alcohol. Initial conversion of propylene oxide is 58%, and selectivity to allyl alcohol is 89%. After 185 hours of operation (including 26 shutdowns and restarts!), conversion of propylene oxide is 47%, selectivity to allyl alcohol is 91.5%, and productivity is about 3 kg allyl alcohol per kg $Li_3PO_4$ per hour.

EXAMPLE 23

The procedure of Examples 5-20 is followed to isomerize 1,2-epoxybutane to crotyl alcohol using 50 wt. % $Li_3PO_4$ supported on "A-14" α-alumina. At WHSV=2.63 h⁻¹, epoxide conversion is 42%, selectivity to crotyl alcohol is 91%, and catalyst productivity is 2.0 kg crotyl alcohol/kg $Li_3PO_4$·h. Results are summarized in Table 4.

EXAMPLE 24

The procedure of Examples 5-20 is followed to isomerize 1,2-epoxyoctane to 2-octen-1-ol using 50 wt. % $Li_3PO_4$ supported on "A-14" α-alumina. At WHSV=2.25 h⁻¹, epoxide conversion is 40%, selectivity to 2-octen-1-ol is 90%, and catalyst productivity is 1.6 kg 2-octen-1-ol/kg $Li_3PO_4$·h. Results are summarized in Table 4.

The preceding examples are intended only as illustrations; the true metes and bounds of the invention are defined by the following claims.

TABLE 1

Gas-Phase Isomerization of Propylene Oxide to Allyl Alcohol Using Supported Lithium Phosphate Catalysts[a]

| Ex. # | Catalyst Support | Type | WHSV[b] (h⁻¹) | % PO Conversion | Allyl alcohol Selectivity[e], % | 1-Propanol Selectivity | Productivity[c], kg AA/kg Li₃PO₄·h |
|---|---|---|---|---|---|---|---|
| 5 | α-alumina | neutral | 2.3 | 56 | 89 | 0.8 | 3.0 |
| 6 | mordenite[d] | neutral | 3.1 | 55 | 87 | 1.0 | 4.0 |
| 7 | Y-zeolite[d] | neutral | 2.3 | 73 | 89 | 0.8 | 4.0 |
| C8 | MgO | basic | 2.3 | 22 | 67 | 6.0 | 0.87 |
| C9 | CaO | basic | 2.3 | 12 | 15 | 40 | 0.10 |
| C10 | γ-alumina | acidic | 2.0 | 48 | 15 | 8.0 | 0.39 |

[a]All catalysts contain 37 wt. % Li₃PO₄ based on the weight of the supported catalyst. Catalysts are prepared by the method of Examples 1-4. Reaction temperature: 300° C.
[b]Weight hourly space velocity in kilograms of propylene oxide feed per hour per kilogram of catalyst.
[c]Productivity measured at reaction time = 20 hours.
[d]Sodium-exchanged support.
[e]The remaining non-selective products are propionaldehyde, acetone (about 2:1 molar ratio) and acrolein (trace).

TABLE 2

Gas-Phase Isomerization of Propylene Oxide to Allyl Alcohol Effect of Lithium Phosphate Loading with α-Alumina as a Support[a]

| Ex. # | Li₃PO₄ Wt. % | WHSV[b] (h⁻¹) | % PO Conversion | Allyl alcohol Selectivity[d], % | 1-Propanol Selectivity | Productivity[c], kg AA/kg Li₃PO₄·h |
|---|---|---|---|---|---|---|
| C11 | 0 | 2.0 | 2.5 | 30 | 1.0 | 0.006 |
| 12 | 12.5 | 2.6 | 26 | 87 | 0.7 | 4.6 |
| 13 | 25 | 2.3 | 48 | 87 | 0.7 | 3.9 |
| 14 | 37 | 2.3 | 56 | 89 | 0.8 | 3.0 |

TABLE 2-continued

Gas-Phase Isomerization of Propylene Oxide to Allyl Alcohol
Effect of Lithium Phosphate Loading with α-Alumina as a Support[a]

| Ex. # | $Li_3PO_4$ Wt. % | $WHSV^b$ ($h^{-1}$) | % PO Conversion | Allyl alcohol Selectivity[d], % | 1-Propanol Selectivity | Productivity[c], kg AA/kg $Li_3PO_4$ · h |
|---|---|---|---|---|---|---|
| 15 | 50 | 2.2 | 60 | 90 | 0.9 | 2.4 |
| C16 | 62.5 | 1.9 | 67 | 91 | 1.1 | 1.9 |
| C17 | 77 | 1.9 | 80 | 91 | 1.1 | 1.8 |

[a] Catalysts are prepared by the method of Examples 1–4. Reaction temperature: 300° C.
[b] Weight hourly space velocity in kilograms of propylene oxide feed per hour per kilogram of catalyst.
[c] Productivity measured at reaction time = 20 hours.
[d] The remaining non-selective products are propionaldehyde, acetone (about 2:1 molar ratio) and acrolein (trace).

TABLE 3

Gas-Phase Isomerization of Propylene Oxide to Allyl Alcohol
Effect of Lithium Phosphate Loading with Sodium-Exchanged Y-Zeolite as a Support[a]

| Ex. # | $Li_3PO_4$ Wt. % | $WHSV^b$ ($h^{-1}$) | % PO Conversion | Allyl alcohol Selectivity[d], % | 1-Propanol Selectivity | Productivity[c], kg AA/kg $Li_3PO_4$ · h |
|---|---|---|---|---|---|---|
| 18 | 25 | 3.12 | 50 | 80 | 0.40 | 5.0 |
| 19 | 37 | 2.34 | 73 | 89 | 0.80 | 4.1 |
| 20 | 50 | 2.38 | 72 | 90 | 0.60 | 3.1 |

[a] Catalysts are prepared by the method of Examples 1–4. Reaction temperature: 300° C.
[b] Weight hourly space velocity in kilograms of propylene oxide feed per hour per kilogram of catalyst.
[c] Productivity measured at reaction time = 20 hours.
[d] The remaining non-selective products are propionaldehyde, acetone (about 2:1 molar ratio) and acrolein (trace).

TABLE 4

Gas-Phase Isomerization of Epoxides to Allylic Alcohols
Using 50 wt. % $Li_3PO_4$ on α-Alumina as a Support[a]

| Ex. # | Epoxide | $WHSV^b$ ($h^{-1}$) | % epoxide Conversion | Allylic alcohol Selectivity[d], % | Productivity[c], kg Allylic alcohol/kg $Li_3PO_4$ · h |
|---|---|---|---|---|---|
| 15 | propylene oxide | 2.20 | 60 | 90 | 2.4 |
| 23 | 1,2-epoxybutane | 2.63 | 42 | 91 | 2.0 |
| 24 | 1,2-epoxyoctane | 2.25 | 40 | 90 | 1.6 |

[a] Catalysts are prepared by the method of Examples 1–4. Reaction temperature: 300° C.
[b] Weight hourly space velocity in kilograms of epoxide feed per hour per kilogram of catalyst.
[c] Productivity measured at reaction time = 20 hours.
[d] The remaining non-selective products are propionaldehyde, acetone (about 2:1 molar ratio) and acrolein (trace).

TABLE 5

Summary of Scanning Electron Micrographs (SEMs)[a,b]

| Figure | Description |
|---|---|
| 1A, 1B | 12.5 wt. % $Li_3PO_4$ on α-alumina |
| 2A, 2B | 25.0 wt. % $Li_3PO_4$ on α-alumina |
| 3A, 3B | 37.0 wt. % $Li_3PO_4$ on α-alumina |
| 4A, 4B | 50.0 wt. % $Li_3PO_4$ on α-alumina |
| 5A, 5B | 62.5 wt. % $Li_3PO_4$ on α-alumina |
| 6A, 6B | 77.0 wt. % $Li_3PO_4$ on α-alumina |
| 7A, 7B | 37.0 wt. % $Li_3PO_4$ on sodium-exchanged mordenite |
| 8A, 8B | 37.0 wt. % $Li_3PO_4$ on sodium-exchanged Y-zeolite |
| 9A, 9B | 50.0 wt. % $Li_3PO_4$ on sodium-exchanged Y-zeolite |

[a] FIGS. 1A–9A are scanning electron micrographs of supported catalyst particles.
[b] FIGS. 1B–9B are phosphorus-mapping SEMs of the same catalyst particles.

I claim:

1. A process for isomerizing an alkylene oxide to an allylic alcohol, said process comprising heating the alkylene oxide in the presence of a supported catalyst, wherein the supported catalyst comprises:
   (a) from about 5 to about 60 percent by weight of lithium phosphate; and
   (b) from about 40 to about 95 percent by weight of an alkali metal-exchanged zeolite.

2. The process of claim 1 wherein the supported catalyst comprises from about 25 to about 40 percent by weight of lithium phosphate and from about 60 to about 75 percent by weight of the alkali metal-exchanged zeolite.

3. The process of claim 1 wherein the alkali metal-exchanged zeolite is an alkali metal-exchanged mordenite.

4. The process of claim 1 wherein the isomerization occurs in the gas phase.

5. The process of claim 4 wherein the process is performed at a temperature within the range of about 180° C. to about 360° C.

6. A process for isomerizing propylene oxide to allyl alcohol, said process comprising heating propylene oxide in the presence of a supported catalyst, wherein the supported catalyst comprises:
   (a) from about 5 to about 60 percent by weight of lithium phosphate; and
   (b) from about 40 to about 95 percent by weight of an alkali metal-exchanged zeolite.

7. The process of claim 6 wherein the supported catalyst comprises from about 25 to about 40 percent by weight of lithium phosphate and from about 60 to about 75 percent by weight of the alkali metal-exchanged zeolite.

8. The process of claim 6 wherein the isomerization occurs in the gas phase.

9. The process of claim 8 wherein the process is performed at a temperature within the range of about 180° C. to about 360° C.

* * * * *